United States Patent [19]
Langevin

[11] Patent Number: 6,156,019
[45] Date of Patent: Dec. 5, 2000

[54] INFECTION RESISTANT BLOOD SAMPLING SYSTEM

[75] Inventor: Paul B. Langevin, Gainesville, Fla.

[73] Assignee: University of Florida, Gainesville, Fla.

[21] Appl. No.: 08/914,194

[22] Filed: Aug. 19, 1997

[51] Int. Cl.[7] .................................................. A61M 1/00
[52] U.S. Cl. .......................................... 604/323; 604/317
[58] Field of Search ................................. 604/4, 52, 53, 604/82, 86, 248, 283, 317, 323, 403; 128/672, 675, 760

[56] References Cited

U.S. PATENT DOCUMENTS

| | | |
|---|---|---|
| 3,057,350 | 10/1962 | Cowley . |
| 3,817,240 | 6/1974 | Ayres . |
| 4,212,308 | 7/1980 | Percarpio . |
| 4,608,996 | 9/1986 | Brown ...................................... 128/760 |
| 4,865,583 | 9/1989 | Tu .............................................. 604/53 |
| 4,981,140 | 1/1991 | Wyatt ....................................... 128/673 |
| 5,151,184 | 9/1992 | Ferkany ................................... 222/514 |
| 5,203,775 | 4/1993 | Frank et al. ............................. 604/256 |
| 5,417,673 | 5/1995 | Gordon ................................... 604/283 |

Primary Examiner—John G. Weiss
Assistant Examiner—David J. Cho
Attorney, Agent, or Firm—Salwanchik, Lloyd & Saliwanchik

[57] ABSTRACT

A device and method for infection-resistant blood sampling from a patient which inhibits passage of microorganisms. The device includes a blood collection mechanism having a one-way valve between a blood collection port and a cannula. The device further includes a second channel with its upstream end in fluid communication with the cannula and its downstream end in communication with the blood collection mechanism.

9 Claims, 7 Drawing Sheets

INFECTION RESISTANT BLOOD SAMPLING SYSTEM

BACKGROUND OF THE INVENTION

As the age of the population continues to escalate and the complexity of the surgical procedures required by these patients increases, the need for invasive hemodynamic monitoring for protracted periods of time continues to expand. Elderly patients suffering from multiple medical illnesses who are status post complex surgical procedures comprise the greatest percentage of occupants in the surgical intensive care units (SICU). These patients are at continued risk of developing overwhelming infections during their stay in the SICU and sepsis continues to be the leading cause of death in this population.

The reason for the increased incidence of infection and sepsis in the SICU patient is multifactorial but includes: immunosuppression, poor nutrition, surgical stress, prolonged intubation, foley catheterization, and the presence of invasive cannulas. Among these, perhaps the most significant are the invasive lines which frequently predispose to the problem commonly known as line sepsis. The magnitude of this problem is greatly under appreciated. If one considers the fact that Maki found only 15 colony-forming units (CFU) present on the catheter were required to precipitate a sepsis in patients with a central line, it is not surprising that large numbers of patients develop this condition. Clearly the longer an invasive cannula is present and the greater the number of such cannula, the more likely an infection is to occur.

Several conditions must be met for a line sepsis to occur and these conditions can be organized into an operational mechanism which results in a line sepsis. First, organisms must enter and then adhere to the cannula. Once localized within the catheter, bacteria remain relatively protected from the patients' defense against infection. Organisms simply injected into a patient can be effectively eradicated by the host while organisms sequestered in the cannula may escape the natural immune defenses of the patient. From this protected nidus, the bacteria can multiply, establish a colony, and spawn generations of organisms. These microorganisms then enter the patient from the line repeatedly if not continuously. While patients may be able to eradicate the small initial numbers of organisms released, as the colony increases in size, they are soon overwhelmed by endlessly increasing numbers of bacteria released, ultimately rendering the patient bacteremic and finally septic.

There are five conditions within this operational mechanism and interrupting any one of them effectively eliminates the potential for infection to occur. Organisms must gain access to the system. The bacteria must be able to adhere to the catheter. There must be a nutrient supply which supports bacterial growth. The bacteria must be able to reach the patient from the location of the colony. The organism must be pathogenic in the numbers reaching the patient. If any one of these requirements were eliminated, this mechanism could not operate and line sepsis could not occur.

There is presently no material available able to prevent adherence of the bacteria to the cannula. Once inside the system, there is no way to preclude their replication if the bacteria are presented with a nutrient supply. Such a nutrient supply will always be present in cannulas which have had blood in them. This results from the fact that residual blood will remain in the catheter once a sample is collected regardless of how carefully the line is flushed. TPN also represents a source of nutrients. Indeed lines never exposed to blood or TPN have a lesser association with sepsis.

The only reasonable way to interrupt this mechanism is to prevent the catheter from being seeded in the first place. Since arterial lines are used to sample blood, there is no way to prevent this residual material from collecting in the system. Furthermore, because these catheters are indwelling and used repeatedly, microorganisms have easy access to the patient once they colonize the system. Virtually any bacteria given in adequate dose will be pathogenic, and current use of antibiotics in hospitalized patients selects for more pathogenic organisms. Hence the only point at which the mechanism can be interrupted is at prevention of inoculation by completely excluding bacteria from entering the system in the first place.

Previously there has been no way to preclude clinicians from introducing the organisms in the currently available OPEN systems. Even when sterile technique is strictly maintained, repetitive manipulation of the line will eventually result in its contamination. The fact that Maki has found that as few as 15 organisms in the catheter can result in a line sepsis clearly demonstrates that introducing even small numbers of bacteria into these systems has profound implications for the patient.

Open systems offer an avenue through which lines can be inoculated with a microorganism, thereby providing a source of contamination which must eventually render a patient septic. Efforts to develop closed systems to address the problem of line sepsis have been made, but have not been readily accepted by clinicians. For example, U.S. Pat. No. 4,865,583 to Tu describes a closed intravenous infusion and blood sampling system comprising a three-way valve and a diaphragm-sealed blood sampling apparatus connected to intravenous infusion and catheter tubing and a flushing syringe having sterilized connections.

U.S. Pat. No. 5,148,811 describes an apparatus and method for sampling blood and monitoring blood pressure wherein positive pressure is utilized to force saline unidirectionally into a patient, and provides a valve for partially reversing the flow, allowing entry of blood into the tubing for sampling, but providing a waste collection bag for preventing return of saline into its source reservoir.

Various other systems have been described for directing blood flow and sampling blood in a manner which reduces the possibility of contamination. See for example U.S. Pat. Nos. 4,981,140; 5,203,775; 5,221,271; and 5,417,673. However, each of the above-described inventions concerns systems that necessarily allow introduction into the system of an exogenous source of potential contamination, effectively representing an open system. In addition, these previously described systems do not provide a means for flushing blood that may be retained in the collection port following blood sampling without also flushing possible contaminants into the cannula where they can multiply unrestrained.

While currently available systems have tried to prevent the injection of contaminated material into the patient, all have failed because they have not addressed the central fact they are open systems. Since the system is open, even for a single event, e.g., sampling blood once from the patient, care givers accessing the line will eventually inoculate it with exogenous microbes, no matter how cautious and meticulous they may be. As an aside it should be remembered that "sterile" technique is really not sterile at all. It simply represents the best attempt possible to exclude microorganisms; the number of organism is only reduced to the lowest level possible. Therefore the line will ultimately be inoculated with small numbers of organisms. Once inoculated the bacteria find an environment replete with nutrients in the form of residual blood. These organisms then multiply in the system. By contrast, the subject invention concerns a system having a one-way valve configured in the blood collection line which prevents entry of any exogenous microorganisms into the cannula. In addition, the subject invention advantageously provides a plurality of channels for diverting flow of fluid from the main cannula line and providing separate and continuous flushing of the blood sampling and monitoring systems.

BRIEF SUMMARY OF THE INVENTION

It is an object of the subject invention to provide a system for preventing entrance of exogenous microorganisms, e.g., bacteria, into the bloodstream of a patient being invasively monitored or treated using an intravenous or intra-arterial cannula. More specifically, it is an object of the subject invention to provide a closed system for blood sampling and monitoring, wherein the system comprises a one-way valve to allow collection of blood from a patient while insuring that no bacteria can enter the system.

It is a further object of the invention to provide a blood monitoring and sampling system having, in series, a blood collection means and a monitor or transducer (e.g., blood pressure monitor), such that a blood sample can be taken, and the residual blood in the line continuously flushed, without contaminating the cannula or line.

DETAILED DISCLOSURE OF THE INVENTION

The system of the subject invention is designed as a closed system effectively preventing the introduction of micro-organisms via the sampling line capable of regardless of the behavior of the care giver. This system is fundamentally different from currently available systems in that those currently used in clinical settings permit inoculation of the system and therefore constitute open systems. The subject invention is closed and can overcome the problems associated with known systems.

Currently, arterial cannulas are used for blood sampling. Once blood enters these lines a nutrient supply exists. Even when the lines are flushed with large amounts of sterile solutions, residual blood products remain and serve as nutrient sources for the scavenging microbes.

Once blood is aspirated into the cannula, residual material represents a nutrient supply even when the catheter is flushed well. Clearly then, once blood is aspirated from a cannula, a nutrient supply is present. The only effective way to prevent bacteria from replicating in the catheter, is to prevent the introduction of organisms into the system in the first place. It is imperative then, that the arterial used for the aspiration of blood samples remain closed.

The design for this system is very simple. A series of one way valves are used to permit aspiration of blood while preventing administration of any exogenous fluid that might contain organisms. Conservation of blood is achieved by reducing the dead space on the sampling line and placing a fixed aspirating syringe proximal (closer to the pressurized reservoir) to the sampling port. Blood in the aspirating syringe can be returned to the patient since it must be sterile. The monitoring line can be flushed in the usual manner. The sampling line is flushed from the proximal reservoir away from the patient.

Figure 2:
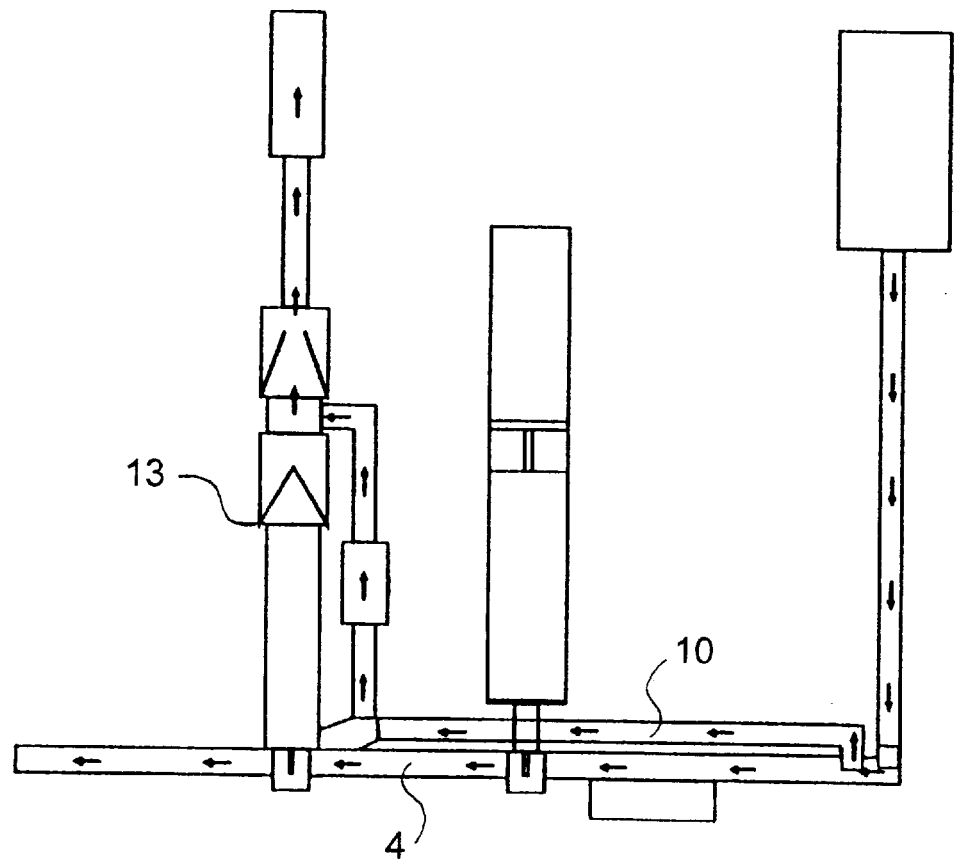
FIG. 2 shows a schematic of the system according to the subject invention in the normal monitoring configuration has the transducer in parallel with the blood sampling system. The figure also shows direction of flow of the fluid (typically heparinized saline) from the fluid source through the cannula (channel 1) and the flushing channel (channel 2) in the standard operation of the system.

Methods of using or operating the system of the subject invention are also shown by the accompanying drawings. For example, in FIG. 2, showing the system as used in the monitoring configuration, heparinized saline flows through the system via the cannula forming the first channel to the patient at a rate of approximately 3 ml/hr. Fluid also flows through the sampling line via a second channel 10 at approximately 1 ml/hr, and is deposited in the collection chamber 18.

Figure 1A:
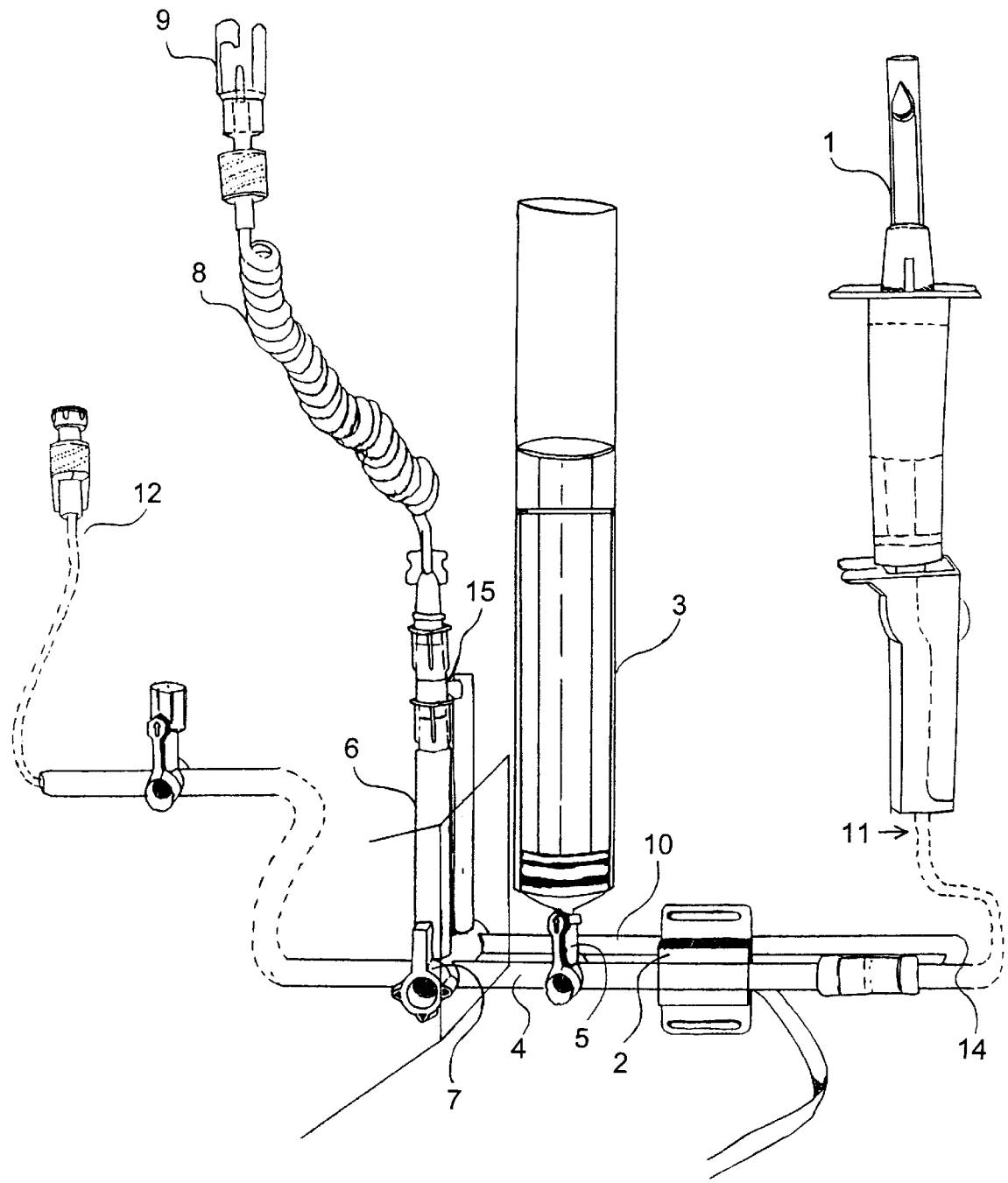
FIG. 1A shows an embodiment of the blood sampling system according to the subject invention. The figure shows an embodiment comprising a fluid source connection means 1, a transducer 2 for connecting to a monitor, a reservoir syringe 3 connected to the cannula 4 via a three-way stopcock 5, a blood collection means 6 connecting to the cannula via a double barreled three-way stopcock 7, the blood collection means comprising a blood collection line 8, a blood collection port 9, and a waste collection chamber (not shown). The embodiment shown in this figure also comprises a second channel 10 which communicates with the conduit to the blood collection chamber through the double barreled stopcock 7.
Figure 1B:
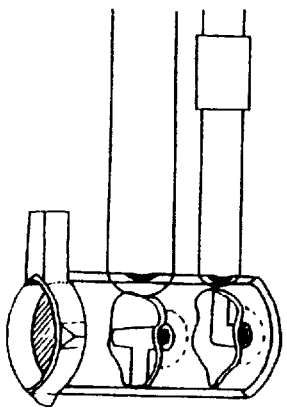
FIG. 1B is a cross section of the embodiment of the blood sampling system shown in FIG. 1A.

The system of the subject invention can perhaps best be understood by reference to the accompanying drawings. FIG. 1 shows a blood sampling and blood pressure monitoring system, according to the subject invention, comprising a cannula 4 for administering a fluid to a patient wherein the cannula has a first end 11 and a second end 12, the first end 11 connectable to a fluid source, e.g., heparinized saline, and the second end 12 connectable to a patient, via a catheter for intra-arterial catheters. Provided in-line along the cannula are a transducer 2 for said blood pressure monitoring in this system, and a blood collection means 6 for collection and sampling of blood from the patient. Positioned between the transducer 2 and the blood collection means is a reservoir 3, into which blood can be drawn upstream from the patient and upstream from the blood collection means.

For purposes of clarity in the instant application, the system is described herein from the first or "upstream" end 11 of the cannula which is connected to the fluid source, to the second or "downstream" end 12 of the cannula which is connected to the patient. The first end of the system can comprise a connecting means for affixing said first end to a fluid source (normally heparinized saline). Preferably, the first end connecting means is a sharpened tip 1, for inserting into a fluid source having standard connecting means for receiving a needle connecting means as is known in the art. The cannula can be of any desired length, so long as the length is ample to conveniently connect the fluid source to the patient while providing for the ports and connections as described herein.

Downstream from the fluid source are connected, in series, a transducer, a reservoir for aspirating blood upstream from the blood collection means, a blood collection means, and the second end, which can be connected to a patient using a standard intra-arterial cannula.

The blood monitoring means can be connected to the system. Blood monitoring means, e.g., blood pressure monitors, are well known in the art to be affixable to the cannula by way of a transducer which can convert or translate pressure signals produced by the blood in the cannula to electrical signals. There are a number of commercially available blood pressure monitors, and currently available models typically provide a digital display of blood pressure. The reservoir system, placed upstream from the blood collection means and downstream from the monitoring system, can in a preferred embodiment comprise a syringe 3 affixed in line with the cannula using a standard three-way stopcock 5. The stopcock 5 is most preferably configured such that it can be alternatively closed to the upstream direction, open to the said reservoir, or closed to the downstream direction and open to the fluid source. Downstream from the reservoir is a blood collection means 6, preferably comprising a blood collection line 8, or catheter, and a double barreled three-way stopcock 7. The double barreled stopcock 7 of the blood collection means, in a preferred embodiment, can be configured such that the stopcock can be alternatively closed to the downstream direction, to the blood collection means, and to the upstream direction. In a more preferred embodiment, as shown in FIGS. 2–5, the blood collection means further comprises at least one-way valve 13 which allows collection of blood from the patient, but does not allow back-flow of fluid from the sampling line, past the valve into the cannula. This one-way valve, necessarily acts as a unidirectional flow inhibitor resisting both back flow of blood and injection of fluids of any kind into the patient. The presence of this one-way valve in the blood collection line can prevent exogenous microorganisms from entering the cannula which would otherwise allow bacteria or other microorganisms to enter the system where they adhere to the components of the system and begin to multiply. Exogenous microbes are thus prevented from entering the system where they can replicate and cause infection, ie the system is closed.

In a most preferred embodiment, as shown in FIG. 1, the subject invention can comprise a second channel 10, having a first end upstream 14 and a second end downstream 15, configured in parallel with the a fore mentioned system. This parallel channel connects to the #11 at a position upstream from the transducer. This second channel can remain open, i.e., in unidirectional communication with the blood collection line, to provide continuous flow from the fluid source to the blood collection means. This channel allows for continuous flow of the fluid 1) which maintains patency of the blood collection line, and 2) flushes organisms away from the patient.

The flow rate of the fluid being administered can be controlled by providing a particular inner diameter of the second channel or other suitable resistor. For example, an inner diameter of approximately 1.0 millimeter can provide approximately 1 milliliter per hour of fluid through the blood collection means. This flow rate can be adjusted by increasing or decreasing as desired the inner diameter of the second channel or alternate resistor. It has been found that a flow rate of approximately 1 milliliter per hour can maintain patency of the blood collection system. In addition, flushing of the blood collection line is achieved by closing the double barrel stopcock 7 to the patient and flushing the system by increasing pressure of the flow in a downstream direction. In a further preferred embodiment, one-way valves can be included both upstream and downstream from the juncture of the second end 15 of the second channel and the blood collection means, thereby creating and defining a flushing chamber 18.

Materials for the system of the subject invention can preferably be a plastic or other polymer which can be sterilized. Other materials known in the art can be used so long as the materials can be subjected to standard sterilization procedures without significant damage to the material or the system. Such materials are well known in the art and are typically used for hospital supplies or other medical devices.

In the system of the subject invention, a series of one-way valves are employed to permit aspiration of blood while preventing administration of any exogenous fluid that might contain organisms. Conservation of blood is achieved by reducing the dead space on the blood collection means and placing a fixed aspirating syringe as a reservoir in close proximity upstream to the collection chamber. Blood in the aspirating syringe can be returned to the patient since it must remain uncontaminated. The monitoring line can be flushed in the usual manner. The blood collection means can be flushed from the reservoir away from the patient. The double barreled stopcock co-ordinates appropriate flow through the two channels, rendering the flow through the system fail-safe.

Figure 3A:
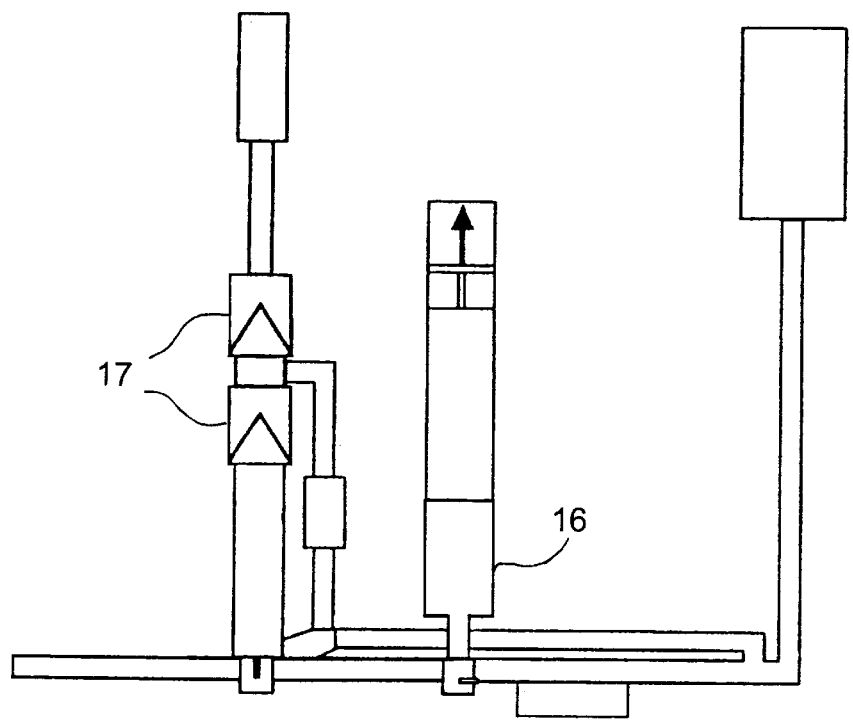
FIGS. 3A and 3B schematically depict steps in the procedure for sampling blood using the system, in accordance with the subject invention.
Figure 3B:
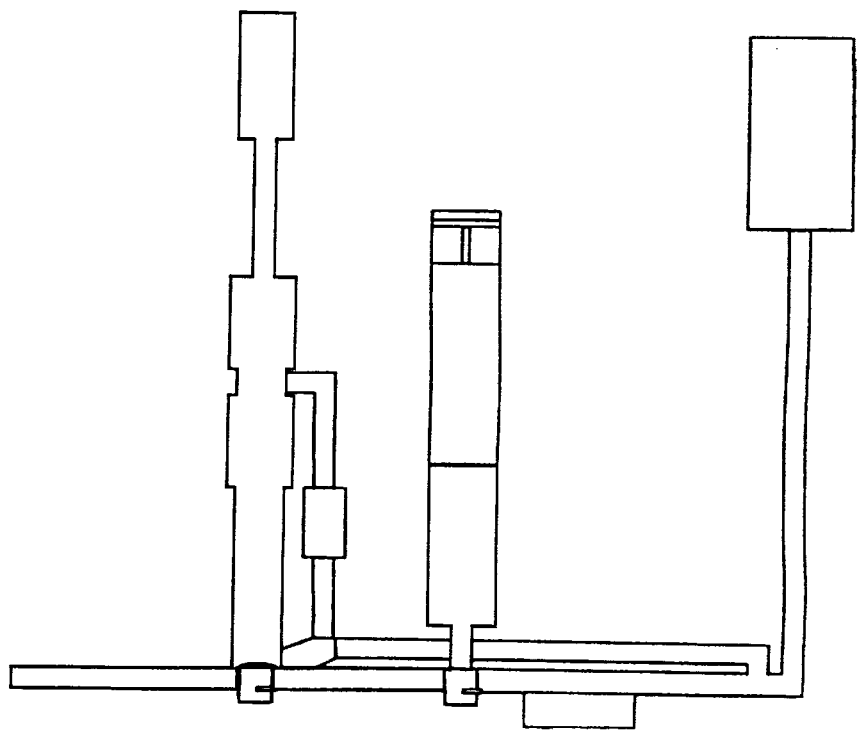

FIG. 3 shows the procedure for sampling blood from a patient. First, a standard three way stopcock 5 joining the reservoir syringe to the cannula can be turned off to the transducer in the upstream direction so that blood can be aspirated into the reservoir syringe 3. A second double barrelled stopcock 7 which joins the cannula and blood collection means is then opened to the patient to permit blood sampling from the patient through the one-way check valves 13 in the blood collection means. The sample is thus obtained while the cannula remains closed at all times to the outside.

Figure 4A:
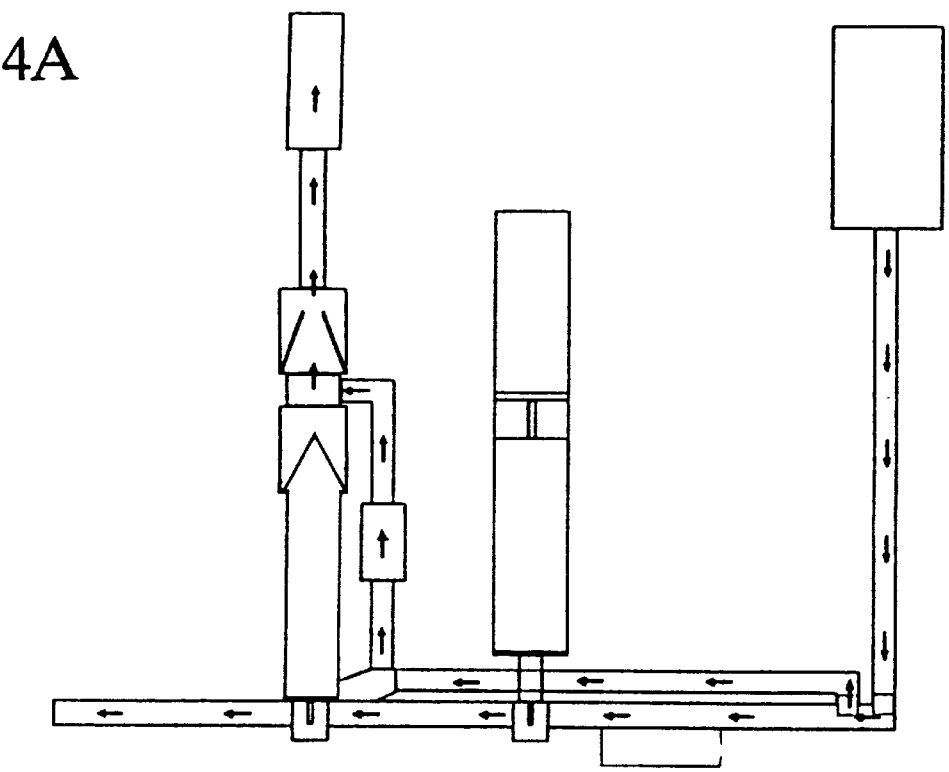
FIGS. 4A–4D schematically depict steps in the procedure of flushing the sampling line of the system in accordance with the subject invention.
Figure 4B:
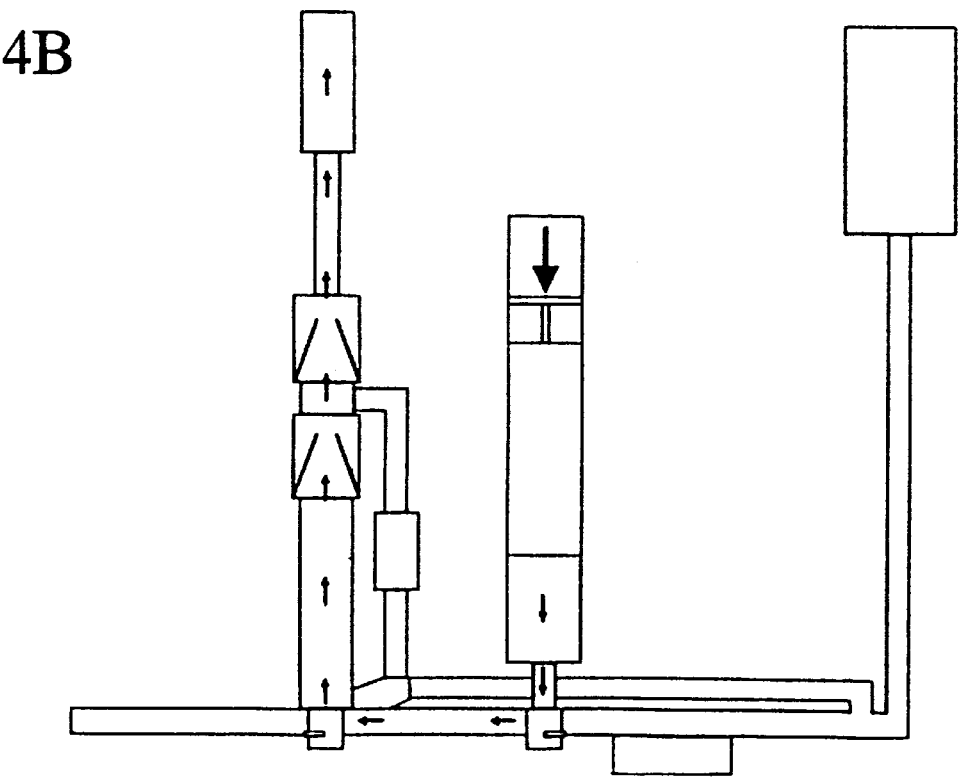
Figure 4C:
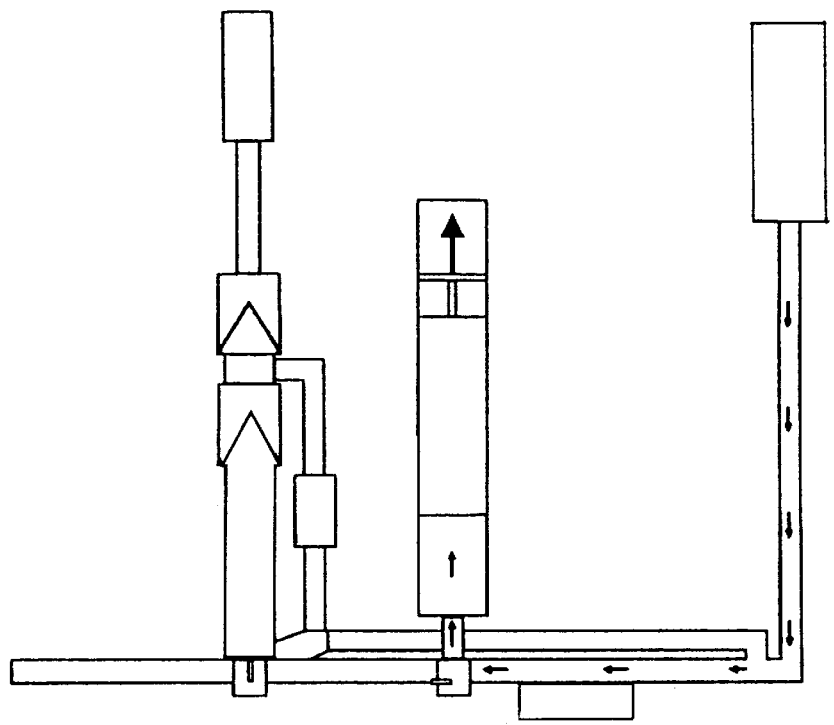
Figure 4D:
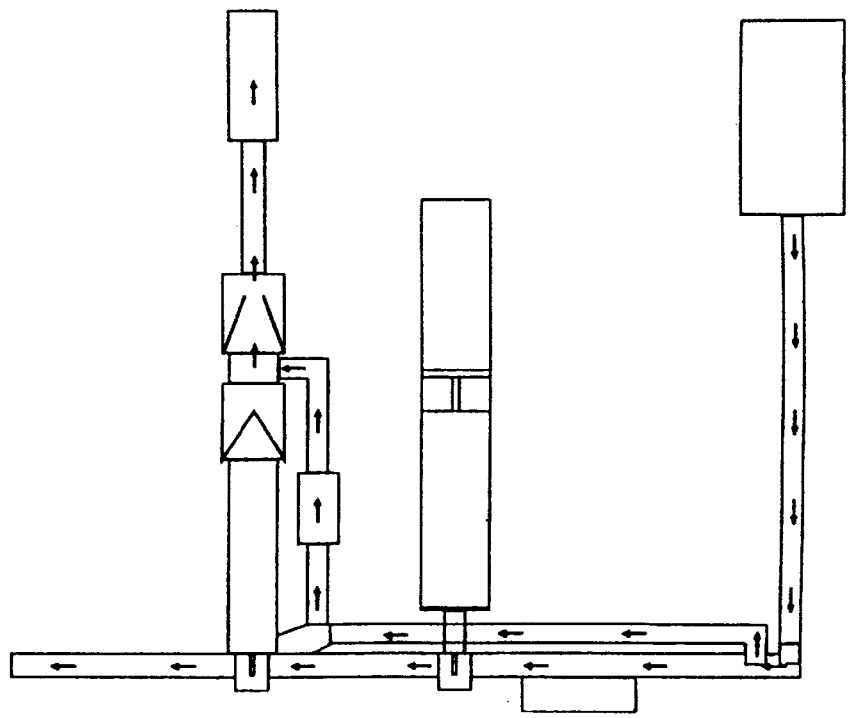
Figure 5A:
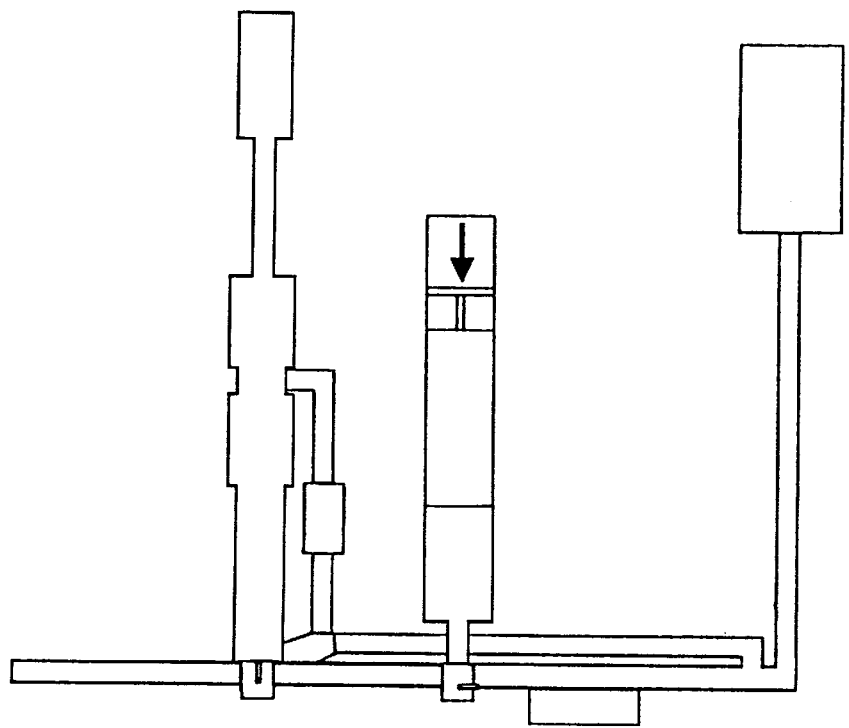
FIGS. 5A–5D schematically depict steps in the procedure for flushing the cannula of the system in accordance with the subject invention.
Figure 5B:
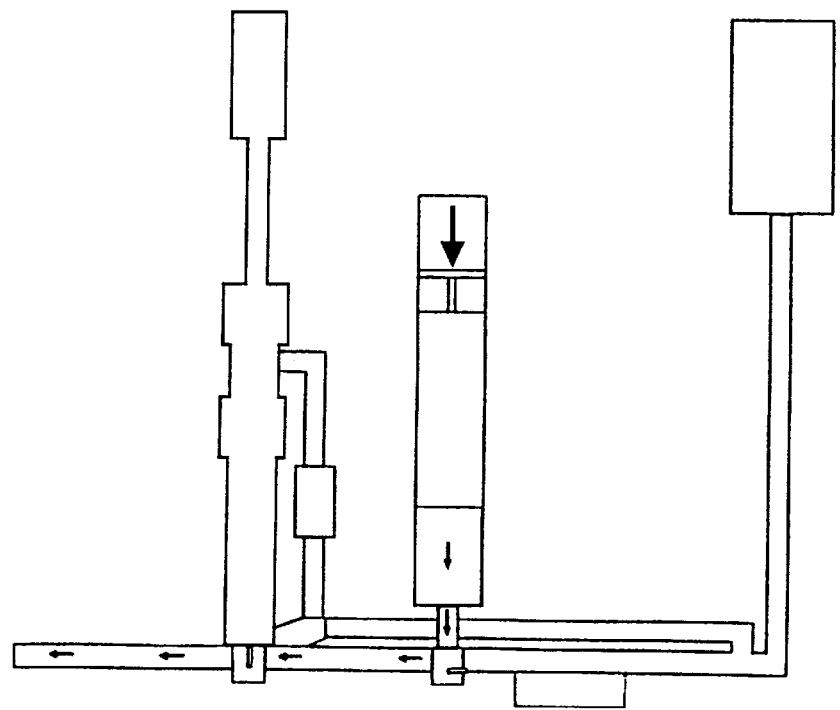
Figure 5C:
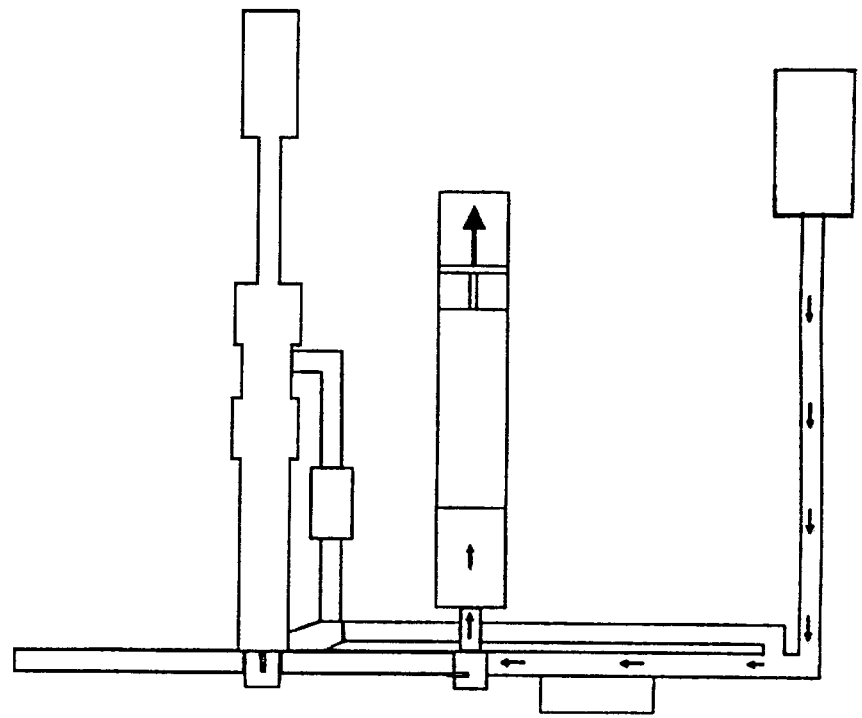
Figure 5D:
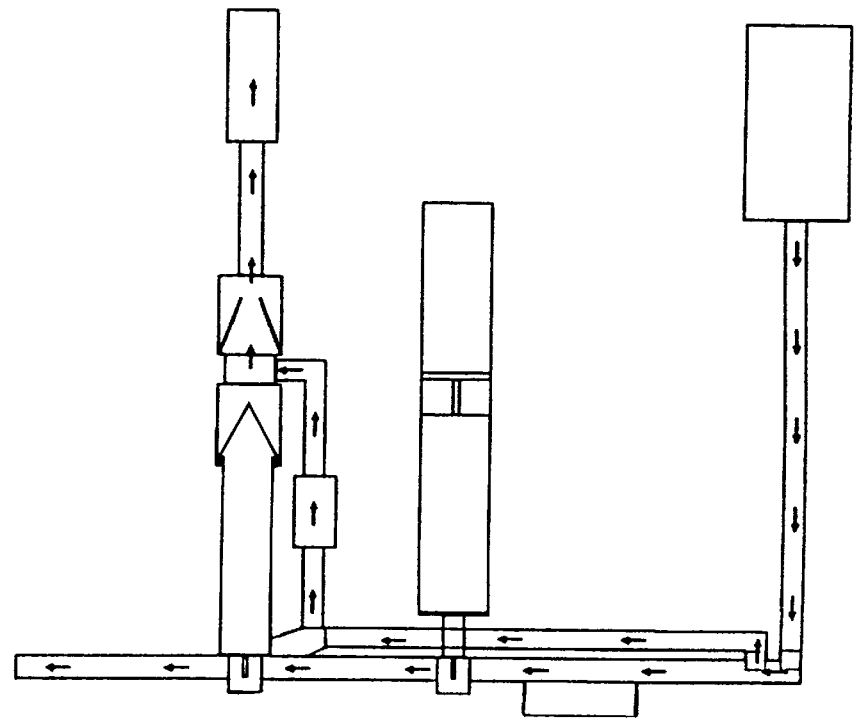

FIGS. 4A–4D and 5A–5D show the procedures for flushing the line after sampling. Specifically, the doubled barreled stopcock 7 can be closed to the sampling line and aspirated blood in the reservoir syringe is returned to the patient. This provides a method for conserving blood during sampling procedures. The first stopcock 5 can then be turned off to the patient, and heparinized saline aspirated into the reservoir syringe (FIGS. 4B and 5B). The first stopcock 5 is then returned to a position which is closed to the transducer. Heparinized saline in the syringe is flushed into the patient clearing the cannula (FIGS. 4C and 5C). Finally, the first stopcock 5 is returned to the operating position to resume blood pressure monitoring.

In the monitoring configuration, the system automatically flushes the blood collection line 8 with 1 ml of heparinized saline per hour. This rate is sufficient to maintain patency since the PVC material used for the collection line is heparin bonded. However, if flushing of the collection line at a rate or volume greater than 1 ml/hr is desirable, the first stopcock 5 can first be turned off to the patient and heparinized saline aspirated into the reservoir syringe. The first stopcock 5 is then turned off to the transducer and the double barreled stopcock 7 is turned off to the patient. Heparinized saline is then flushed from the reservoir syringe into the flushing chamber 18 and out through the collection line. The system is finally returned to the operating configuration (FIG. 2).

Following are examples which illustrate procedures for practicing the invention. These examples should not be construed as limiting.

EXAMPLE 1

Sterility Maintenance by System

The system of the subject invention can be demonstrated to reduce the potential for contamination of the monitoring line. The subject system is designed to guarantee that the patient cannot be inoculated with exogenous microorganisms regardless of the technique or actions of the care giver.

Available studies have shown that a patient should be unequivocally protected from inoculation for about five days with this system. Since most ICU's have strict policies to change lines every three days—some less frequently, but never longer than five days, this represents a substantial increase in the life expectancy of the line and will reduce the number of line changes required in patients requiring long term invasive monitoring.

The exact duration over which sterility is maintained can be determined experimentally. A sterile bag of growth media under pulsatile pressure of 120/80 mmHg can be used to simulate the arterial blood stream. Samples can be withdrawn from the sampling port analogous to obtaining an ABG repetitively every hour. A syringe used to withdraw the "ABG" can be deliberately contaminated with a variety of microorganisms, including gram negative, gram positive, motile, and immotile organisms. Once the "ABG" is obtained, the line is flushed with heparinized saline in the prescribed manner.

Aliquots can be withdrawn from the pulsatile bag of growth media simulating the patient's blood at regular intervals to determine if any bacteria entered the "patient". The presence of even a single contaminating organism will be detected with this method since any viable microorganism will multiply in the media effectively amplifying its presence to the level of detection. The absence of bacteria in the "blood stream" indicates that contamination at the sampling port did not inoculate the line or patient.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. In an intravenous apparatus having a cannula with a first end upstream and a second end downstream, said second end connectable to a patient, a device for infection-resistant blood sampling from the patient, comprising:

a directional valve disposed between said first and second ends of said cannula to selectively direct the flow of blood to a blood collection means in fluid communication therewith, said blood collection means comprising a uni-directional flow inhibitor disposed within said blood collection means between a blood collection port and said valve to inhibit re-entry of fluids into said cannula from said port.

2. The device, according to claim 1, further comprising a reservoir for temporary storing of blood during sampling, said reservoir disposed upstream of said blood collection means, between said blood collection means and said first end of said cannula.

3. The system, according to claim 2, wherein said system further comprises a means for continuous flushing of said cannula without introducing a source of infection.

4. The device, according to claim 3, wherein said flushing means comprises a second channel having a first end upstream and a second end downstream, wherein said first end is in fluid communication with said cannula and said second end communicates with said blood collection means.

5. The device, according to claim 4, wherein said first end of said second channel communicates with said cannula upstream of said reservoir.

6. The device, according to claim 5, wherein said second end of said second channel is in fluid communication with said blood collection means downstream of said uni-directional flow inhibitor.

7. The device, according to claim 6, wherein said blood collection means comprises two uni-directional flow inhibitors, and said second end of said second channel is in fluid communication with said blood collection means between said uni-directional flow inhibitors.

8. A method for infection-resistant blood collection from a patient, said method comprising the steps of:

(a) providing a device of claim 1;

(b) connecting said device to the blood supply of the patient; and (c) drawing blood through said blood collection means.

9. The method, according to claim 8, wherein said method further comprises flushing of said cannula or said blood collection means on a selectable continuous basis.

* * * * *